United States Patent [19]

Wetegrove et al.

[11] Patent Number: 5,155,555
[45] Date of Patent: Oct. 13, 1992

[54] MONITORING OF FILM FORMERS

[75] Inventors: Robert L. Wetegrove, Winfield; Rodney H. Banks, Naperville, both of Ill.

[73] Assignee: Nalco Chemical Company, Naperville, Ill.

[21] Appl. No.: 726,592

[22] Filed: Jul. 8, 1991

[51] Int. Cl.⁵ .................................... G01B 11/06
[52] U.S. Cl. ............................ 356/381; 356/446; 356/448; 356/244; 250/576; 250/341; 250/372
[58] Field of Search .............. 356/36, 38, 70, 445, 356/446, 448, 244, 381, 382; 250/573, 574, 576, 341, 372

[56] References Cited

U.S. PATENT DOCUMENTS

| | | | |
|---|---|---|---|
| 2,489,286 | 11/1949 | Grant, Jr. | 356/38 |
| 3,589,813 | 6/1971 | Sturzinger | 250/574 |
| 4,135,100 | 1/1979 | Harada et al. | 250/573 |
| 4,916,317 | 4/1990 | Gabriel et al. | 356/445 |
| 4,943,735 | 7/1990 | Nishikawa | 250/573 |

Primary Examiner—F. L. Evans
Attorney, Agent, or Firm—Kinzer, Plyer, Dorn McEachran & Jambor

[57] ABSTRACT

Method and apparatus for measuring film formers in an opaque process stream by immersing a disc in the fluid stream, allowing time to accumulate film formers, then rotating the disc to expose the previously immersed section to optical monitoring by which a sample reflectance and a reference reflectance are compared.

8 Claims, 2 Drawing Sheets

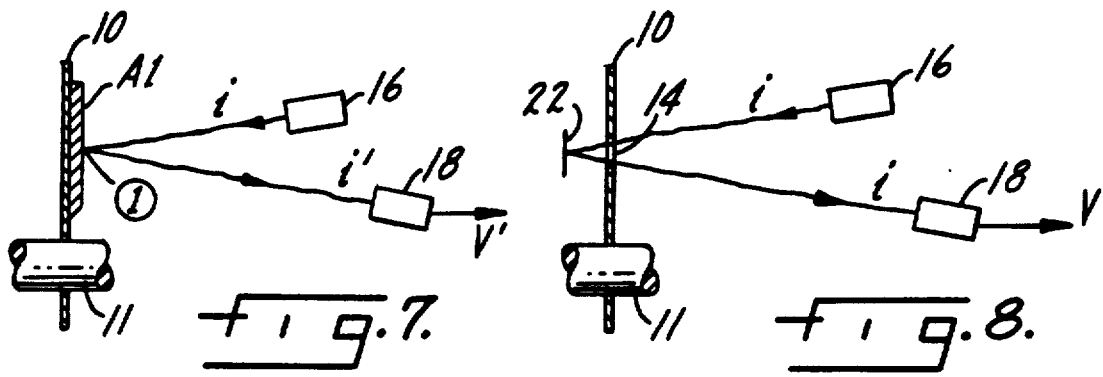
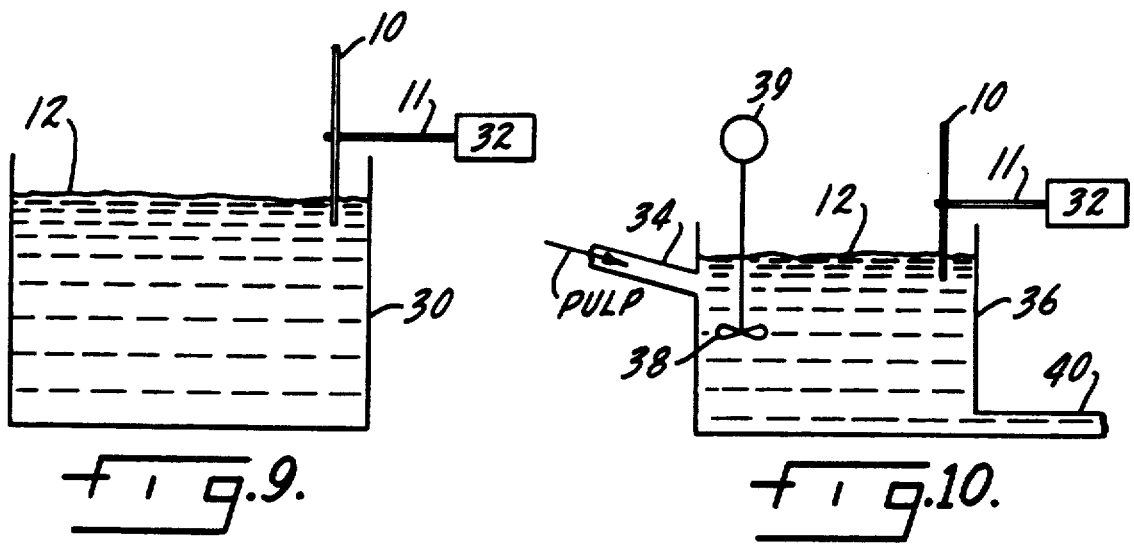
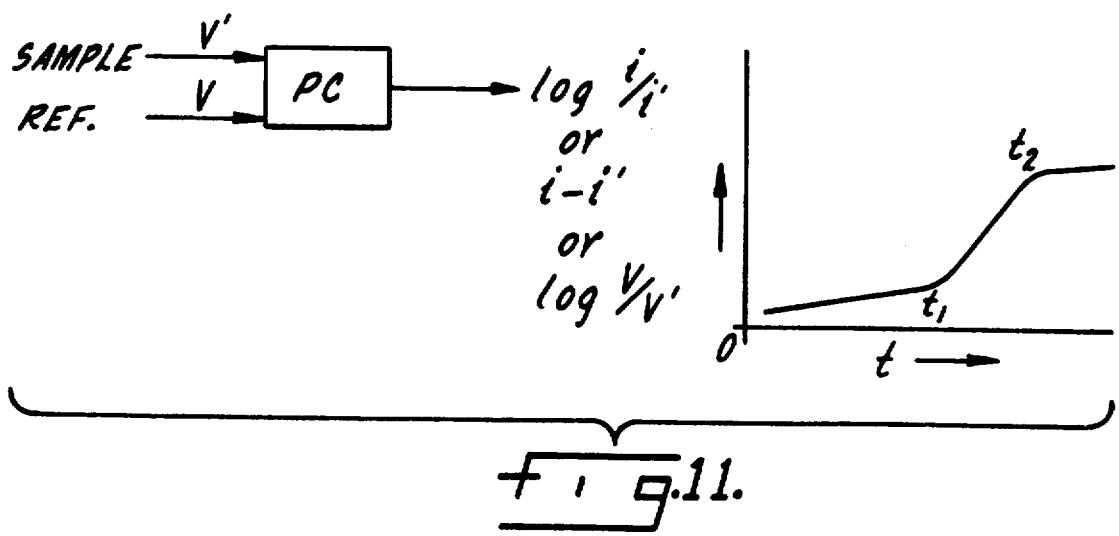

MONITORING OF FILM FORMERS

BACKGROUND OF THE INVENTION

This invention relates to the determination of unwanted deposit formations in an opaque fluid stream employed for industrial or manufacturing processes. Determination is made in situ or by real time analysis, or near to it, rather than by extracting a sample of the fluid for external laboratory analysis elsewhere.

There are numerous examples of industrial fluid streams confined by a conduit for manufacturing purposes where entrained biological growths or organic impurities deposit on and reduce the efficiency of equipment employed in processing the fluid. Not only that, the finished product may be contaminated by the film.

A good example is paper making machinery when the confining conduit is the paper machine itself. Bacteria colonies, protozoa and other simple life forms become entrained in the pulp. These feed and thrive on indigenous substances such as proteins, oils, carbohydrates and polysacharides. The colony expands and becomes a gummy, sticky biofilm which can trap other particles and deposit on the walls of the chest and other equipment in the pulp confining conduit downstream of the chest. The equipment becomes fouled. Not only that, the unwanted films are loosened due to turbulence and become part of the paper, resulting in grade degradation. Pitch (hydrophobic contaminants) present as part of the wood fibers is another source of an unwanted organic deposits.

The same phenomena are involved in cutting oils as another example. The purity and efficiency of the oil are degraded, the surfactant which maintains the cutting oil as an emulsion is adversely affected, and film deposits on the workpiece being machined.

In our co-pending application Ser. No. 07/754,016, filed Sep. 3, 1991 we address the problem of film formers in a transparent process stream such as cooling tower water, undertaking a double beam transmittance comparison (reference and sample) to detect film buildup. In the present invention, we address the same problem (film growth or build-up) in an opaque stream where light transmittance is difficult if not impossible to measure accurately. Instead, we use light reflectance as will be explained.

SUMMARY OF THE INVENTION

Reflected light is employed to determine film occurrences in an opaque fluid stream confined by a conduit employed in processing that stream for manufacturing purposes. Since the stream is opaque, light transmittance values cannot be depended upon. We therefore immerse in the stream a surface (disc, coupon) of such nature as to accumulate the film which adheres to the immersed surface, remove the surface to expose the adherent film, and monitor the film on the exposed surface by reflected light, the intensity of which is an analog of film thickness. If the thickness exceeds a predetermined allowance, a microprocessor will activate a pump which feeds to the stream a treating agent which disperses or controls film former(s).

In more specific terms, the invention is characterized by a disc or equivalent configuration which may be of homogeneous material but preferably contains discrete segments presenting surfaces of different materials. The disc is partly submerged in the opaque process stream and is supported for rotation. If rotated by a stepping motor, the disc may be turned at selected intervals so that the segment previously immersed is exposed for monitoring by an optical sensor which measures the intensity of light (originated from a source) reflected (reflectance) from one or more targeted areas containing the film sample. Less light is reflected from a spot or target having greater film thickness. The exposed surface may be indexed by the stepping motor so that multiple spots on the disc may be targeted, obtaining an average of reflectance readings of accumulated fouling.

By maintaining immersion for a relatively long-term period, the immersed segment simulates exposure of the equipment (process conduit and attendant parts) to long term or passive accumulations of fouling. Then, by immediately rotating the disc after taking a long-term average of reflectance, or even a single reflectance reading corresponding to long-term immersion, the fresh segment may be monitored as a short-term wetted surface simulating turbulent or mere wetting film conditions. This difference between passive and wetting film conditions can be of significance. The passive film may be taken as one in which the bacterial identity or growth conditions are not severe or pernicious, that is, the film build-up is slow. In comparison, the segment which is immersed for a short term will capture the most tenacious or pernicious film formers such as organic pitch, one of the more inimical deposit formers.

PRIOR ART

To the best of our knowledge there is no art pertinent to the present invention characterized by reading reflectances from a disc having successive long and short term immersions in an opaque fluid containing film formers which adhere to one portion of the disc, simulative of less innocuous or passive film formers, and adhere to another portion of the disc simulative of strong or pernicious film former.

There are systems for detecting internal film formation, namely, U.S. Pat. Nos. 4,912,332 and 3,757,210 but these disclosures do not comply with the characterizing features of the present invention.

BRIEF DESCRIPTION OF THE DRAWING

FIGS. 7 and 8 are schematic views of the optic reflectance principles which feature in the present invention;

FIGS. 9 and 10 are schematic views of the invention in practice; and

FIG. 11 is a diagram showing measurement of film thickness, an analog of film thickness vs. time.

BEST MODE: INSTRUMENTATION

Characterization of the present invention is best explained in terms of the schematics shown in the various figures.

Figure 1:
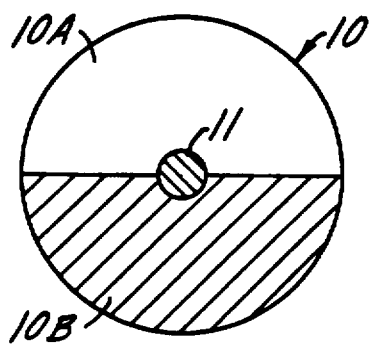
FIG. 1 is a diagram of a disc illustrating its division into hydrophilic and hydrophobic segments.

A disc 10, FIG. 1, rotatably secured to a shaft 11 is preferably divided into two segments which need not necessarily be of the same area. Segment 10A presents a ferrous metal surface (deemed hydrophilic) to simulate typical process equipment such as employed in a paper mill for the so-called machine chest (chest) and other equipment which tends to be fouled by organic film formers. Ideally, the disc would be of stainless steel and segment 10A therefore is preferably stainless steel, but it is sufficient that segment 10A will indeed tend to accumulate the film former proportional to the equipment exposed to the process fluid which is deemed opaque for purposes of light transmittance.

The other segment 10B presents a hydrophobic surface, preferably TEFLON ® resin.

Figure 2:
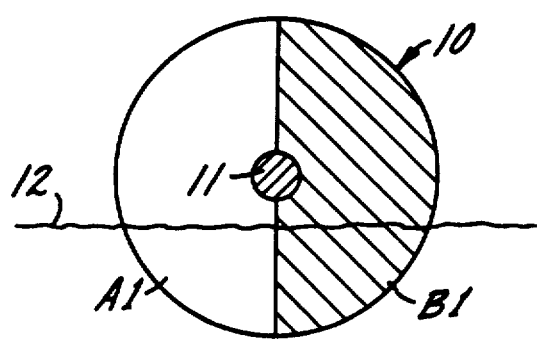
FIGS. 2 through 6 are diagrams of different positions to be assumed by the disc when partly submerged in an opaque fluid to be sampled.

Now, if the disc is rotated counterclockwise 90°, FIG. 2, and partly immersed in an opaque fluid having a surface level 12 (e.g. the paper pulp in the chest of a paper making machine), the immersed portion will include a metal or hydrophilic section A1 and a hydrophobic section B1. If this combination is maintained for many hours or even days, both sections will tend to be contaminated by the deposit formers which are present. Specifically, the hydrophobic section will accumulate such organics as oils and pitches while the metal section A1 will accept the bacterial film former sources.

Figure 3:
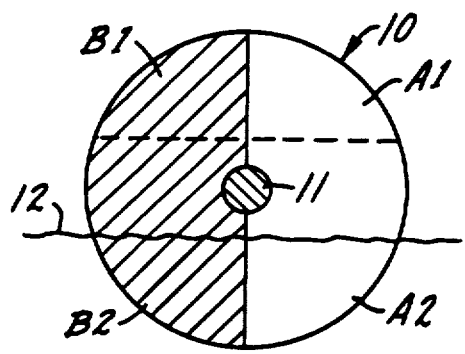

If the disc is rotated 180° counterclockwise to the FIG. 3 position, both sections A1 and B1, previously immersed, are elevated exposed about level L. The area above the dashed line denotes the (now elevated) area that was immersed, and these elevated areas can be monitored optically as will be explained in more detail below to determine quantitatively (by reflectances) the thickness of the films in those portions of areas A1 and B1 which underwent long-term immersion.

During optical monitoring of the previously immersed portions of sections A1 nd B1, sections A2 and B2 are immersed. This is only for a few minutes or so, after which the disc is rotated counterclockwise another 180° so that sections A2 and B2 are now exposed for optical monitoring, FIG. 4, where again the dashed line shows the limit of immersion. Now, sections A2 and B2 can be checked or analyzed optically for the most tenacious film formers, those having the strongest tendency to cling to the equipment.

Figure 4:
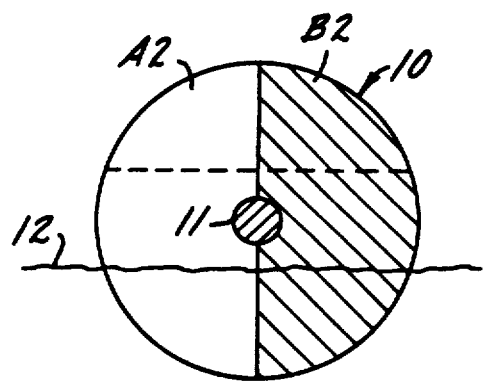
Figure 5:
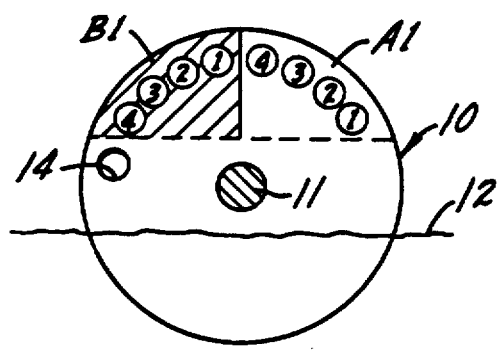
Figure 6:
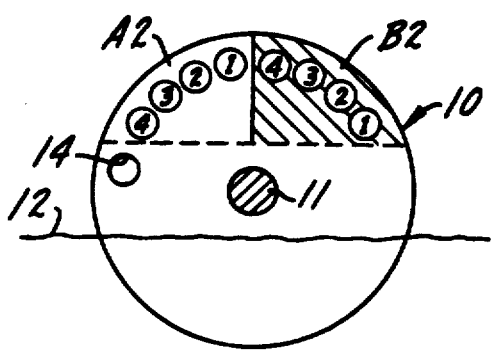

Referring now to FIGS. 5 and 6, these correspond to FIG. 3 (long-term immersion) and FIG. 4 (short-term wetting) and are simplified to show only the immersed areas to be monitored, A1 and B1 (from FIG. 3) and A2 and B2, from FIG. 4. Also, in FIGS. 5 and 6 the encircled digits (1,2,3,4) designate radial spots o targets to be monitored and averaged; but there could be more or fewer targeted spots depending upon circumstances in the field.

The disc 10 has a radially positioned hole 14 which serves as the source of a reference reflectance as will be explained.

BEST MODE: DETAILS

According to Beer's Law, the light absorbed by an absorbing material is proportioned to its thickness. This law allows the thickness of the film on the disc to be measured by casting a light beam of known intensity i on to the film, and measuring the intensity of the light reflected back which of course will be of less intensity, i'. By comparison (i-i') or (i'/i) the difference or ratio is a measure of the film thickness.

Referring to FIG. 7, the disc 10, after long term immersion, has been rotated to a position corresponding to FIG. 5, and at this position target 1, FIG. 7, in section A1 is presented to a light source (IR or UV) 16 which casts or directs a beam of intensity i on target 1, A1. A sensor 18 responds to the reflected light, intensity i', which can be converted to a voltage analog V'.

A programmer, not shown, then activates the stepping motor to index the disc clockwise so that the opening 14, FIG. 8, is presented to the light source 16. The same beam (intensity i) is cast or directed through the opening 14 and is reflected by a clean or pristine surface 22 (e.g. clean stainless steel) to the sensor 18 as the reference intensity value i, eliminating any drift. In effect the reference intensity i (at 14) undergoes no absorbance.

Reflectance from reflector 22 results in an up-dated reference each time it is indexed to reflect the intensity of the light source. Without the reference for each reading, there could be considerable drift or deviation of light from source 16 due to temperature changes, humidity changes, dust on the optics and so on.

The sensor 18 converts the reflectance intensity i' to a voltage analog V'.

The two analogs can be compared by a computer and by difference (V-V') or ratio (V'/V) the thickness of the film, target spot 1, is determined.

The measurements can be repeated sequentially for targets 2, 3 and 4, section A1, likewise for all the targets in section B1. Each sequence includes presenting the opening 14 to eliminate drift for all readings. By so doing, an average of film thickness can be taken for section A1, which simulates bio-fouling build-up on the equipment, and likewise an average film thickness on the hydrophobic section B1 which simulates entrainment of organics such as pitches and oils in the process stream.

Following an analysis of the long-term immersion, the stepping motor will be actuated to rotate disc 10, 180° from the FIG. 5 position to the FIG. 6 position so that the short term immersion conditions may be monitored in the same manner for segments A2 and B2.

Except for the reference surface 22, less light will always be reflected when a film is present. However, the basic comparison is light intensity, reflected light of intensity i' compared to the reference intensity i.

In the instance of monitoring a paper pulp stream, the disc 10 could be immersed in the so-called water or machine chest 30, FIG. 9, shaft 11 being indexed by a stepping motor 32. However, the paper pulp stream to be monitored could be drained by a pipe 34, FIG. 10, to a separate test or sampling tank 36 where turbulence is simulated by an impeller 38 driven by a motor 38. The return line is indicated by reference character 40 assuring true flow and process conditions.

PROGRAMMING

The monitor system described above can be computer controlled. The following program would be typical:

1. Stepping motor idle, disc position FIG. 3 and hold 24 hours.
2. At 24:00 step disc to FIG. 5 position and energize light source 16 to target spot 1-A1.
3. At 1-A1 read i' and store i'; actuate stepping motor to index opening 14 for targeting by light source 16 and read i reflected by surface 22.
4. Actuate stepping motor to position target 2-A1 to receive light beam from source, read i' and store i'.
5. Actuate stepping motor to index opening 14 to path of light beam source and read intensity i of light reflected by the clean or pristine surface 22.
6. Repeat indexing of remaining spot films 3 and 4 in segment A (and reference reflectances) and store values of i' for each step.
7. Repeat steps 3-6 for disc section B1 and separately store values of i'.

8. After completing the foregoing, say at time 00:30, actuate the stepping motor to turn disc from FIG. 5 to FIG. 6 position and monitor film thickness at B2 (1-4) and A2 (1-4) with intervening referencing to eliminate drift.

DATA PROCESSING

The reflectance (intensity i') readings are constantly calibrated or corrected for drift, but there may be circumstances where only one reading at each section A1 and B1, FIG. 5, will be sufficient, equally so for sections A2 and B2, FIG. 6. However, an average is better and consequently multiple readings for each segment will be taken to obtain an average i'.

In any event, the significant datum, each time, is the difference or ratio of i and i' which can be a voltage analog (millivolts, mv) representing film thickness. Thus, as shown in FIG. 11, the voltages V' (sample) and V (reference) emitted by the detector 18, FIGS. 7 and 8, can be microprocessed at PC to determine the absorbance value for each reading, namely, $$\text{Absorbance (Abs)} = \log i/i' = \log V/V'$$

Since absorbance is proportional to film thickness and is proportioned to i/i', the microprocessor can be programed to resolve any of the analogs by which the intensity of the reflected sample light is compared to the reference intensity i reflected by the reference surface 22. This equivalency of values is shown by the computer print-out or display in FIG. 11 where the equivalents of film thickness are represented by the vertical coordinate values. The horizontal coordinate is time t. From this print-out or screen display the tendency for film build-up can be followed. Typically, film thickness increases gradually (arithmetically) to $t_1$ and then accelerates (exponentially) $t_1$ to $t_2$ which calls for a correction by injecting a treating agent to combat the deposited matter. Other analogs of film thickness are possible (vertical axis, FIG. 11) but voltage is by far the easiest to process.

We claim:

1. Method of monitoring film formers in an opaque fluid comprising:
   (a) immersing in the fluid a segment of a disc having a surface to which the film formers will occlude;
   (b) rotating the disc after a predetermined time of immersion to expose for optical monitoring the previously exposed segment containing the occluding film;
   (c) casting a light beam on an area of the exposed occluding film to be sampled for thickness and measuring the intensity of the light reflected therefrom as the sample reflectance;
   (d) measuring the intensity of the same light beam reflected from a clean surface as the reference reflectance;
   (e) and determining the difference between the reference reflectance and the sample reflectance as a measure of film thickness.

2. Method according to claim 1 in which the disc has at least two segments presenting surfaces which differ in kind respectively to occlude film formers which differ in kind and subjecting each segment to steps (c), (d) and (e).

3. Method according to claim 2 in which the disc is a ferrous metal disc, one segment presenting a surface which is hydrophilic in character and a second segment presenting a coating which is hydrophobic in character.

4. Method according to claim 1 in which the sample and reference reflectances are converted to voltage analogs V' and V respectively, and in which the voltage analogs are ratioed, log V/V', as the absorbance of the film equivalent to film thickness.

5. Method according to claim 4 in which log V/V' is plotted as a function of time.

6. Apparatus positioned adjacent a body of liquid for determining the tendency for opaque film formers, entrained in the body of liquid, to produce build-up on equipment exposed to the liquid and comprising: a rotatable disc having a lower portion immersed in the liquid body to occlude an opaque film originated by the entrained film formers whereby upon rotation of the disc the occluded film is exposed above the body of liquid for measurement, a source of light of known intensity i to be cast onto the elevated occluded film as a target and a sensor to measure the intensity i' of light reflected by the target, said source of light and said sensor being located above the body of liquid at one side of said disc, and means to compare the two intensities i and i' as an analog measure of film thickness on the disc.

7. Apparatus according to claim 6 in which the disc has one segment presenting a hydrophilic surface to occlude hydrophilic film formers and a second segment presenting a surface to occlude hydrophobic film formers.

8. Apparatus according to claim 6 including means to convert the intensities i and i' to a voltage analog ratio as a measure of film thickness.

* * * * *